United States Patent
Martz

[19]

[11] Patent Number: 6,162,457
[45] Date of Patent: *Dec. 19, 2000

[54] PERSONAL PERFUME APPLICATION METHOD AND SYSTEM

[76] Inventor: Christine Martz, 1128 Ruth Pl., North Bellmore, N.Y. 11710

[ * ] Notice: This patent issued on a continued prosecution application filed under 37 CFR 1.53(d), and is subject to the twenty year patent term provisions of 35 U.S.C. 154(a)(2).

[21] Appl. No.: 09/149,805

[22] Filed: Sep. 8, 1998

[51] Int. Cl.[7] ............................. A61L 15/46; D03D 3/00; B32B 7/12
[52] U.S. Cl. ..................... 424/448; 428/905; 428/354; 428/42.1; 424/449
[58] Field of Search ..................... 428/905, 354, 428/42.1; 424/448, 449

[56] References Cited

U.S. PATENT DOCUMENTS

| | | | |
|---|---|---|---|
| 4,038,239 | 7/1977 | Coyner et al. | 260/33.6 UB |
| 4,321,117 | 3/1982 | Kaetsu et al. | 204/159.16 |
| 4,447,590 | 5/1984 | Szycher et al. | 528/76 |
| 4,483,759 | 11/1984 | Szycher et al. | 204/159.24 |
| 4,614,787 | 9/1986 | Szycher et al. | 528/75 |
| 4,824,707 | 4/1989 | Spector | 428/905 X |
| 4,880,690 | 11/1989 | Szycher et al. | 428/224 |
| 4,917,920 | 4/1990 | Ono et al. | 428/905 X |
| 5,050,910 | 9/1991 | Schechter et al. | 283/105 |
| 5,071,704 | 12/1991 | Fischel-Ghodsian | 428/354 |
| 5,242,521 | 9/1993 | Hibsch et al. | 156/200 |
| 5,338,548 | 8/1994 | Kochinke et al. | 424/449 |
| 5,341,992 | 8/1994 | Bishopp | 239/34 |
| 5,389,174 | 2/1995 | Hibsch et al. | 156/200 |
| 5,391,420 | 2/1995 | Bootman et al. | 428/195 |
| 5,399,404 | 3/1995 | Laughlin et al. | 428/905 X |
| 5,455,043 | 10/1995 | Fischel-Ghodsian | 424/448 |
| 5,503,332 | 4/1996 | Glenn | 428/905 X |
| 5,569,683 | 10/1996 | Bootman et al. | 523/102 |
| 5,610,072 | 3/1997 | Scherl et al. | 436/96 |
| 5,622,263 | 4/1997 | Greenland | 206/581 |
| 5,637,401 | 6/1997 | Berman et al. | 252/315.2 |
| 5,744,209 | 4/1998 | Parkes | 428/96 |

FOREIGN PATENT DOCUMENTS

| | | | |
|---|---|---|---|
| 0188883 | 7/1986 | European Pat. Off. | A61M 35/00 |
| 2034728 | 6/1980 | United Kingdom | G08G 18/14 |

*Primary Examiner*—Daniel Zirker
*Attorney, Agent, or Firm*—Alfred M. Walker

[57] ABSTRACT

A user-worn fragrance emitting patch is worn with the fragrance emitting absorbent pad side facing the skin of the user, and the adhesive side is placed adjacent to the inside of the user's clothing. Therefore, the constant on and off touching of the fragrance emitting side to the skin of the user allows the perfume to contact the body oils of the user, thereby emitting an odor which is muted and softer than the original pungent odor of the fragrance.

12 Claims, 3 Drawing Sheets

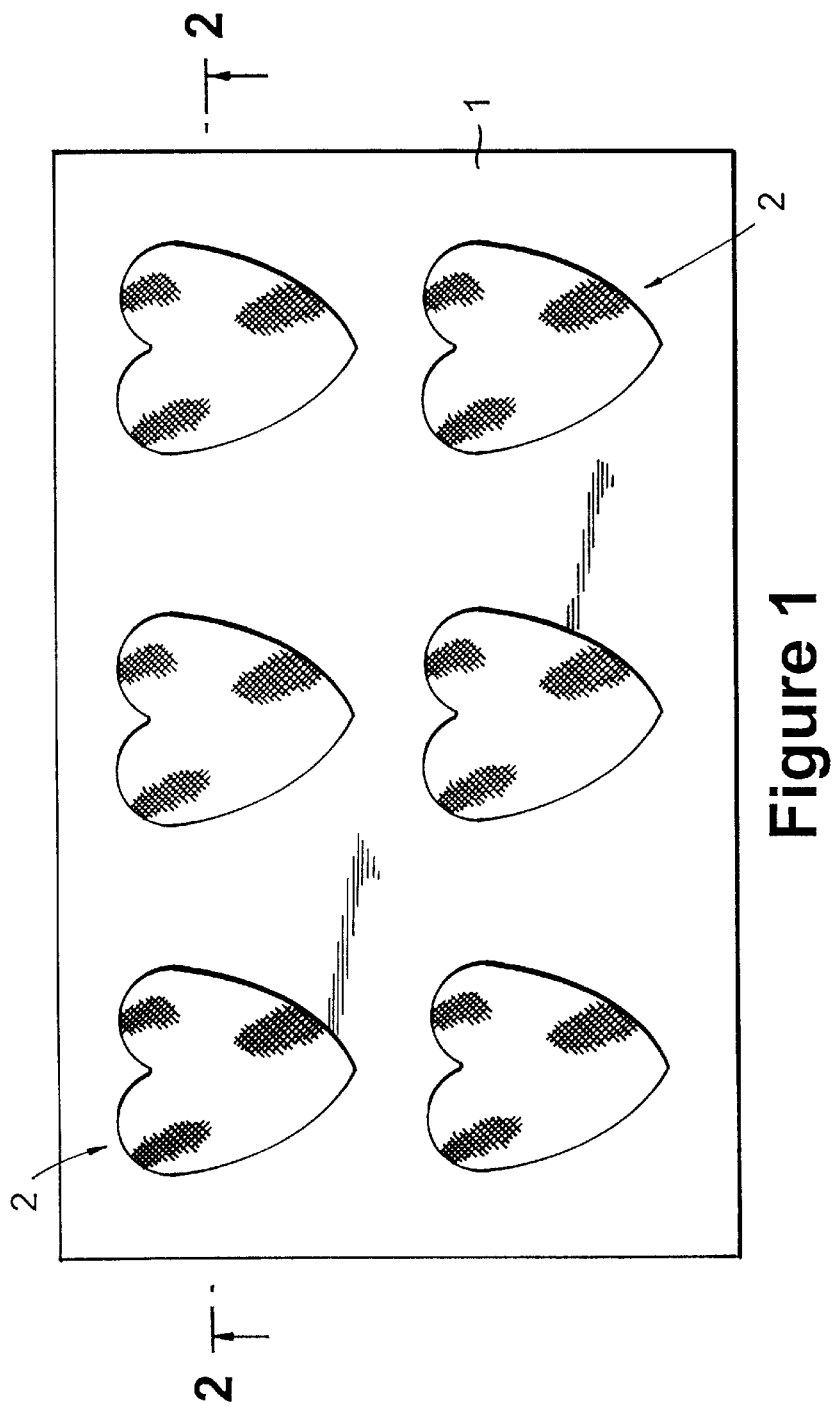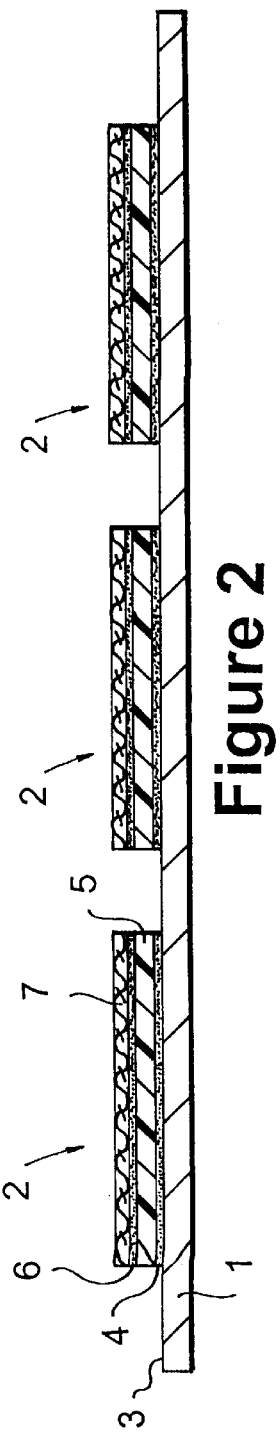

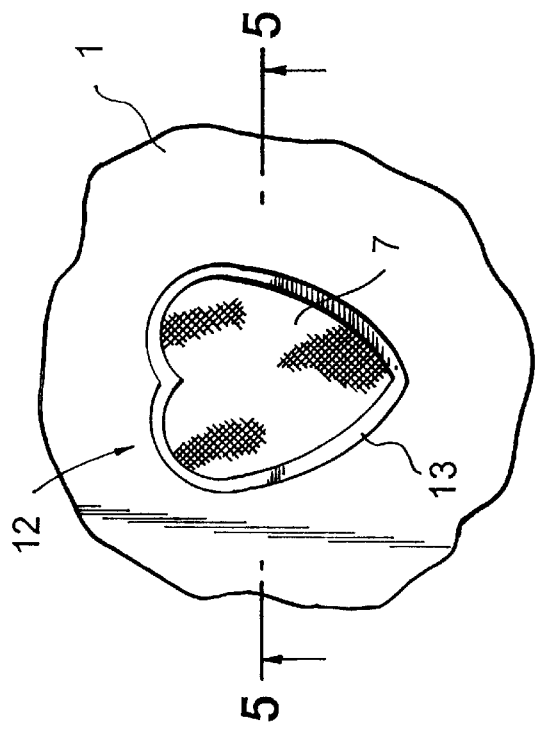
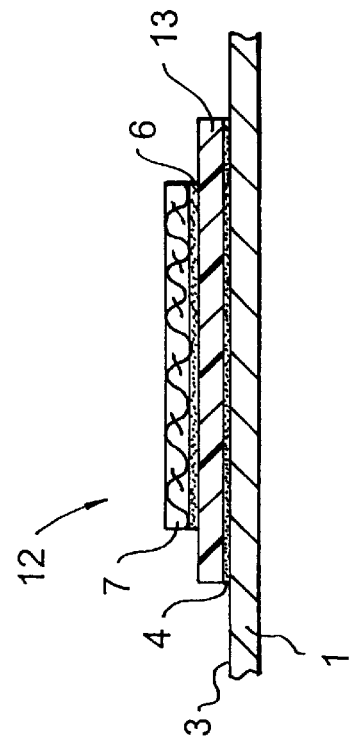
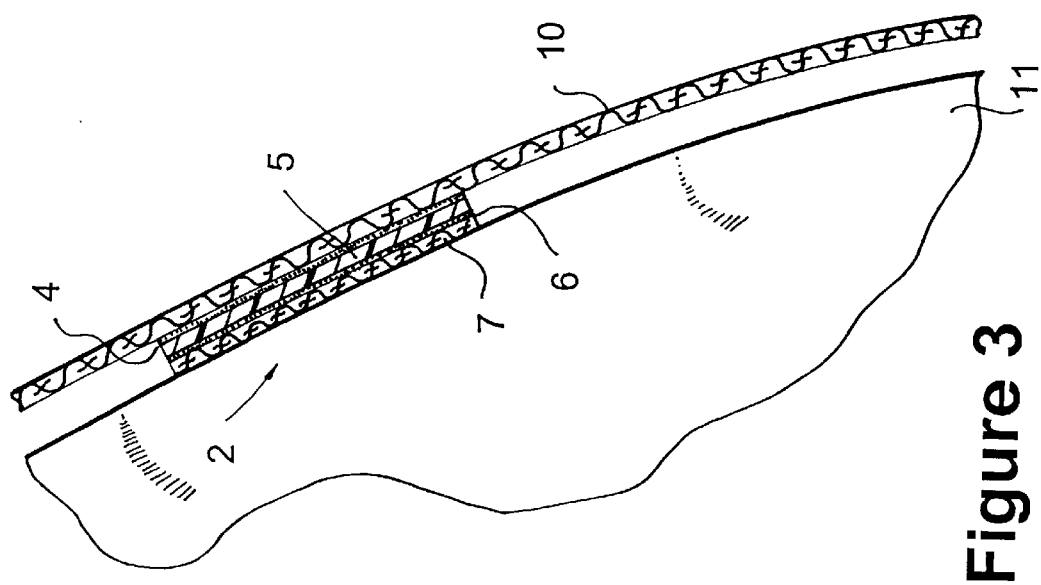

PERSONAL PERFUME APPLICATION METHOD AND SYSTEM

FIELD OF THE INVENTION

The present invention relates to user-worn fragrance dispensing devices.

BACKGROUND OF THE INVENTION

One problem faced by users of fragrances, such as perfume or cologne is to wear a fragrance that is emitted at the desired level over an extended period. Applying an amount of a fragrance, such as perfume, directly to the skin such that the initial desired level of fragrance is achieved usually results in inadequate levels after a period of time as short as two hours. By applying a greater amount to compensate for this loss, the initial level of fragrance is overpowering while the duration of the desired level is only extended for a short time period.

The prior art reveals some attempts at the solution to this or related problems. It is well known that various solid substrates such as waxes or polymeric materials have been impregnated with fragrance and used as room air fresheners. A process for the manufacture of a foam containing a particulate filler and a fragrance is described in UK Patent application 2 034 728 entitled "Polyurethane Foam Products Having Controlled-release Fragrance". European Patent application number 65309014.0 of Charbonneau entitled "Pad Fragrance Sampling Device" relates to microencapsulated materials used in creating samples of fragrance which are released by pulling apart a layer. The fragrance is then simultaneously temporally applied in a conventional manner.

U.S. Pat. No. 4,880,690 of Szycher et al. describes a multi-layer perfume patch member for timed release of fragrance. It is intended that the user adhere this patch to the skin by a layer of pressure sensitive adhesive to emit a desired level of fragrance outwardly away from the skin of the user and directly from the perfume patch, over an extended period by a controlled time-release mechanism.

However, in Szycher '690, the fragrance is emitted directly from the perfume patch to the ambient air, and does not make direct contact with the skin. The scent is therefore identical to that of an open bottle of the same fragrance, which can be sometimes quite pungent.

The chemistry of perfumes is such that they smell different on different people depending on several individual parameters. For example, it has been found that personal pH balance, composition of body oils, and even diet have an effect on the smell sensation evoked by a particular perfume on a particular person, when that perfume is applied directly to the skin and mixes directly with body oils of the user. Some perfumeries even perform a pH test on a customer as a starting point in helping with initial perfume selection. It is therefore well know that perfume as applied to skin smells distinctly different from the smell of an open bottle of the same perfume, since the user's body oils soften the pungent odor of the perfume so that when emitted the smell of the perfume is muted and more pleasant. A favorite perfume is often the result of much individual testing and personal experience.

The prior art does not provide a solution to the dilemma of a consumer attempting to find a method of using their favorite perfumes in such a manner as to provide their familiar scent in a muted odor over an extended period within a range of acceptable potency.

OBJECTS OF THE INVENTION

An object of the present invention is to provide a method by which a consumer can select their own fragrance, such as perfume, and use it in such a manner as to provide a desired level of fragrance over an extended period.

Another object of the present invention is to permit the fragrance, such as perfume to mix with skin components in a normal fashion to achieve the desired individual fragrance characteristics.

Yet another object of the present invention is to provide a pad which will not saturate garments with fragrances, such as perfume, possibly producing stains.

It is yet a further object of the present invention to provide a system and device for muting the pungent odor of a fragrance by causing the fragrance to mix with the user's own body oils.

It is still another object of the present invention to provide an easily manufactured inexpensive personal fragrance dispensing system that is convenient to use, compact, and reliable.

It is yet another object of the present invention to improve over the disadvantages of the prior art.

SUMMARY OF THE INVENTION

In keeping with these objects and others which may become apparent, the present invention is a user-worn fragrance emitting patch which is worn with the fragrance emitting side facing the skin of the user, and the adhesive side being adjacent to the inside of the user's clothing. Therefore, the constant on and off touching of the fragrance emitting side to the skin of the user allows the perfume to contact the body oils of the user, thereby emitting an odor which is muted and softer than the original pungent odor of the fragrance.

The present invention incorporates the use of a layered absorbent pad that is adhered to the inside of a garment. Perfume is applied to the pad by the user prior to attachment to the garment. The fragrant surface of the applied pad faces the user's skin such that normal mixing of perfume with skin elements takes place at the interface. Normal random motions between the skin and the pad surface permit the fragrance to slowly permeate over an extended period. It has been demonstrated that three puffs of a typical pump spray on a pad of 1.0 to 1.5 square inches (6 to 10 square cm) will provide sufficient perfume for a period of six to eight hours.

BRIEF DESCRIPTION OF THE DRAWINGS

The present invention can best be understood when viewed in conjunction with the accompanying drawing figures, in which:

FIG. 1 is a top view of a card with six decorative fragrance emitting pads of the present invention;

FIG. 2 is a side view cross section view of the card as in FIG. 1 with fragrance emitting pads;

FIG. 3 is a side view in cross section detail of a fragrance emitting pad of the present invention in use;

FIG. 4 is a top view detail of alternate embodiment of a fragrance emitting pad of the present invention;

FIG. 5 is a side view in cross section of an alternate embodiment for a fragrance emitting device.

DETAILED DESCRIPTION OF THE INVENTION

Figure 6A:
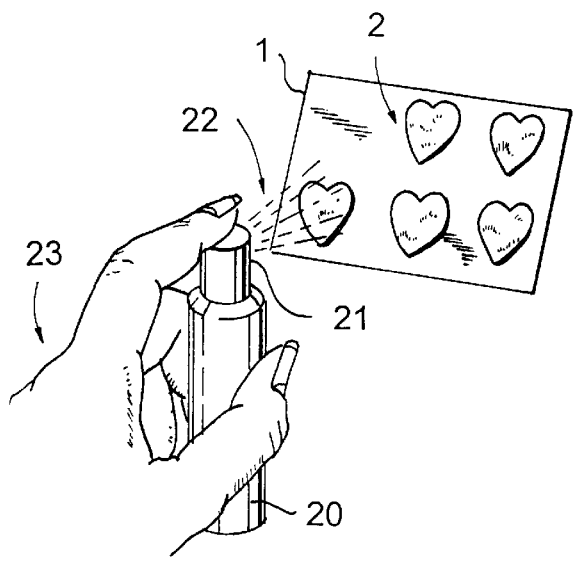
FIGS. 6A, 6B, 6C and 6D are four perspective views illustrating one method of applying fragrance to and using the fragrance emitting pads of the present invention as a sequence of operations.

FIG. 1 shows a card 1 with a plurality of decorative pads 2, such as, for example, six decorative pads 2 in the shape of hearts. Any decorative shape that present an area of from about 1.0 to 1.5 square inches (6 to 10 square cm) is preferable. Example shapes can be geometric (such as diamonds or stars) or any other fanciful composition including company trademarks or character indicia or shapes.

FIG. 2 shows a cross section of FIG. 1 taken along at lines A—A. The card 1 can be a paper layer, such as 50 pound kraft, or a thicker layer, such as cardboard, which may be easier to handle due to its rigidity. The important aspect of card 1 is that surface 3 should be treated to represent a release surface to adhesive layer 4. A common release coating is silicone. Layer 4 is a hypoallergenic pressure sensitive adhesive that will be used to attach pad 2 to the underside of a garment. An acrylate adhesive such as that used on 1530 nonwoven medical tape from 3M® Medical Specialty Products can be used.

This adhesive layer 4 is coated on barrier impermeable layer 5 which is preferably polypropylene, but any impermeable layer compatible with adhesive layers 4 and 6 and resistant to the solvent qualities of fragrances, such as perfumes, may be used. Adhesive 6 may be the same as adhesive 4 or it would preferably be an adhesive with higher tack (or adhesion) than adhesive layer 4 to attach layer 5 to layer 7.

The top fragrance emitting layer 7, is preferably a medical grade spun or woven cotton or cotton/nylon blend, forming a fragrance retaining reservoir. A foam pad, such as polyurethane foam, can also be used as top fragrance emitting layer 7. The relative layer thicknesses of layers 5 and 6, as shown in FIG. 2, are not representative, but they are chosen for clarity of the illustration.

FIG. 3 is a cross section detail view of one of the fragrance emitting pads 2 in use. Adhesive layer 4 attaches fragrance emitting pad 2 to the underside of a garment 10 while top fragrance emitting layer 7 is in intimate contact with a layer of skin 11 on the user's body 12. At a different moment in time, the contact between top fragrance emitting layer 7 and the skin 11 may be lost, permitting the fragrance to escape this interface.

FIG. 4 shows an alternate embodiment 12 of perfume pad wherein the barrier layer 13 extends beyond the periphery of the top fragrance emitting layer 7. This provides better protection to insure that perfume from the wetted fragrance emitting layer 7 is not transferred to the garment to which it is attached.

FIG. 5 shows a cross section view of this arrangement for a fragrance emitting pad as shown in FIG. 4.

While the fragrance can be applied to the fragrance emitting layer 7 during manufacturing, in an alternate embodiment, the fragrance emitting pads 7 can be supplied empty, so that the user applies the predetermined quantity of fragrance just prior to use. For example, FIGS. 6A, 6B, 6C and 6D illustrates this alternate method of applying and of use of this perfume pad system. The illustration shows the application of the pad to the underside of one of the cups of a brassiere. The garment chosen is for illustration only; the use of the perfume pad is in no way restricted to this type of garment. It simply shows one application that is possible; the essential aspect is that the pad 2 be attached to a garment in such a manner that the top fragrance emitting layer 7 can contact the user's skin.

In the illustration of FIG. 6A, the user's hand 23 is shown operating pump spray 21 atop perfume bottle 20. An aerosol applicator can be used as well; perfume liquid drops can also be applied to pad 2. Spray 22 is directed at lower left pad 2 on card 1.

Figure 6B:
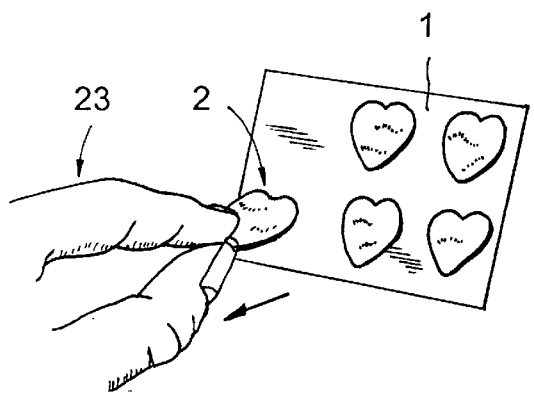

In the illustration of FIG. 6B, the user's hand 23 is shown peeling off pad 2 (which was wetted in FIG. 6A) from card 1.

Figure 6C:
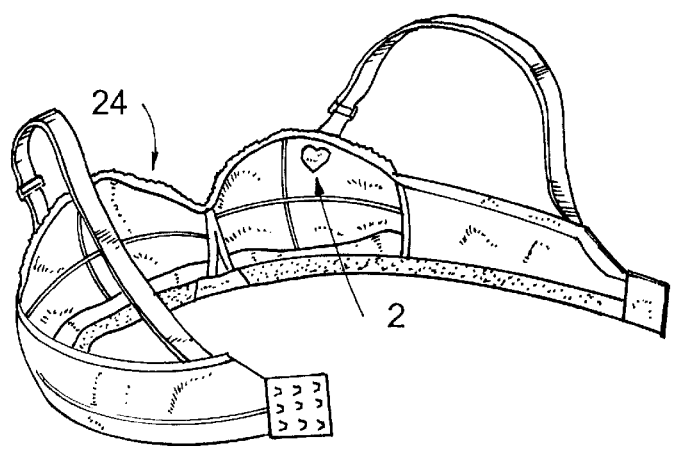

The illustration of FIG. 6C shows pad 2 attached to the inside of a cup of brassiere 24.

Figure 6D:
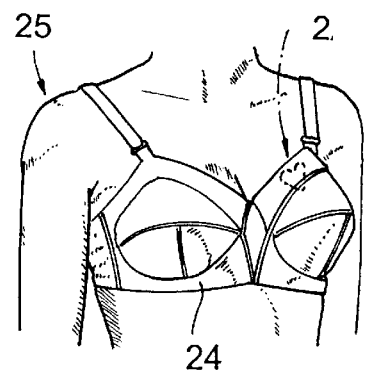

The illustration of FIG. 6D shows brassiere 24 as worn on torso 25 with a phantom view of fragrance emitting pad 2.

User-worn fragrance emitting patch 2 is then worn with the fragrance emitting layer 7 facing the skin 11 of the user, and the adhesive layer 4 is adjacent to the inside of the user's clothing. Therefore, the constant on and off intimate contact of the fragrance emitting layer 7 of fragrance emitting patch 2 to the skin 11 of the user allows the perfume therein to temporally and intermittently contact the body oils of the user, thereby emitting an odor which is muted and softer than the original pungent odor of the fragrance in fragrance emitting pad 2.

It is further noted that other modifications may be made to the present invention, without departing from the scope of the present invention, as noted in the appended Claims.

I claim:

1. A user-worn fragrance emitting patch in combination with an article of clothing worn by a user comprising:

an article of clothing worn by a user having an exterior surface and an inside skin facing surface;

a fragrance emitting layer facing absorbent pad in contact with the bare skin of the user, said pad being mounted on a base having an adhesive side being mounted on said inside skin-facing surface of said article of clothing of the user with said absorbent pad facing said bare skin and said absorbent pad being in intermittent temporal contact with said bare skin;

said fragrance emitting absorbent pad forming a fragrance retaining reservoir retaining a predetermined quantity of odor emitting fragrance therein to the bare skin of the user;

wherein said fragrance contacts the bare skin of the user and mixes with the body oils of the user, wherein further said fragrance emitting absorbent pad containing said fragrance emits an odor which is muted and softer than an original pungent odor of the fragrance.

2. The user-worn fragrance emitting patch as in claim 1 wherein said article of clothing having said skin facing surface is an undergarment worn on the upper part of the body of said user.

3. The user-worn fragrance emitting patch as in claim 1 wherein said absorbent pad facing said bare skin is from about 1.0 to 1.5 inches square.

4. The user-worn fragrance emitting patch as in claim 1 wherein said base of said absorbent pad facing said bare skin is cut from a paper layer.

5. The user-worn fragrance emitting patch as in claim 1 wherein said base of said absorbent pad facing said bare skin is cut from cardboard.

6. The user-worn fragrance emitting patch as in claim 1 wherein said absorbent pad facing said bare skin bears a predetermined fanciful shape.

7. The user-worn fragrance emitting patch as in claim 1 wherein said absorbent pad facing said bare skin bears a predetermined trademark indicia.

8. The user-worn fragrance emitting patch as in claim 1 wherein said absorbent pad facing said bare skin bears a predetermined character shape.

9. The user-worn fragrance emitting patch as in claim 1 wherein said absorbent pad facing said bare skin comprises cotton.

10. The user-worn fragrance emitting patch as in claim 1 wherein said absorbent pad facing said bare skin comprises polyurethane foam.

11. A method of applying and using a fragrance emitting patch by a user comprising the steps of:

applying a predetermined quantity of a liquid fragrance to an absorbent pad of a patch having a fragrance emitting skin facing side and an adhesive garment adhering side;

removing a release liner from said adhesive side of said fragrance emitting patch;

attaching said fragrance emitting patch to an underside skin facing side of a garment being worn by and in contact with the bare skin of an upper part of the body of said user; and allowing said absorbent pad containing said liquid fragrance in direct contact with the bare skin of said user to temporarily and intermittently release an odor to the bare skin of the user in intimate contact with the skin of the user, thereby emitting an odor which is muted and softer than the original pungent odor of said liquid fragrance.

12. The method of claim 11 in which said garment having said skin facing surface is an undergarment.

* * * * *